United States Patent [19]

Wehinger et al.

[11] Patent Number: 4,703,119
[45] Date of Patent: Oct. 27, 1987

[54] INTERMEDIATES OF OPTICALLY ACTIVE 1,4-DIHYDROPYRIDINES

[75] Inventors: Egbert Wehinger, Wuppertal, Fed. Rep. of Germany; Horst Meyer, West Haven, Conn.

[73] Assignee: Bayer Aktiengesellschaft, Leverkusen, Fed. Rep. of Germany

[21] Appl. No.: 741,099

[22] Filed: Jun. 4, 1985

[30] Foreign Application Priority Data

Jun. 22, 1984 [DE] Fed. Rep. of Germany ....... 3423105

[51] Int. Cl.[4] .................. C07D 207/50; C07D 401/12; C07D 403/12; C07D 405/12
[52] U.S. Cl. .................................. 540/544; 540/553; 540/575; 540/597; 540/598; 540/601; 540/602; 540/603; 544/58.5; 544/141; 544/238; 544/283; 544/335; 544/336; 544/363; 544/364; 544/366; 544/367; 544/368; 544/369; 544/370; 544/371; 544/373; 544/353; 546/145; 546/147; 546/172; 546/174; 546/199; 546/201; 546/208; 546/209; 546/210; 546/211; 546/281; 546/249; 546/321; 546/193; 546/196; 546/197; 546/198; 548/126; 548/204; 548/214; 548/217; 548/236; 548/241; 548/247; 548/249; 548/327; 548/336; 548/374; 548/467; 548/517; 548/518; 548/527; 548/557
[58] Field of Search .............. 546/249, 321, 145, 147, 546/172, 174, 193, 196, 197, 198, 199, 201, 208, 209, 210, 211; 548/518, 557, 126, 204, 214, 217, 236, 241, 247, 249, 327, 336, 374, 467, 517, 527; 540/601, 603, 602, 544, 575, 553, 597, 598; 544/58.5, 141, 238, 283, 335, 336, 363, 364, 366, 367, 368, 369, 370, 371, 373, 353

[56] References Cited
U.S. PATENT DOCUMENTS 4,510,310  4/1985  Wehinger et al. .................. 546/321

OTHER PUBLICATIONS

Shibanuma et al., Chem Pharm Bull., 28(9), pp. 2809–2812 (1980).
Enders, D. et al., Tetrahedron, vol. 40, No. 8, pp. 1345–1359 (1984).
Enders, D. and Papadopoulos, K., Tetrahedron Letters, vol. 24, No. 45, pp. 4967–4970 (1983).

Primary Examiner—Henry R. Jiles
Assistant Examiner—Dale A. Bjorkman
Attorney, Agent, or Firm—Sprung Horn Kramer & Woods

[57] ABSTRACT

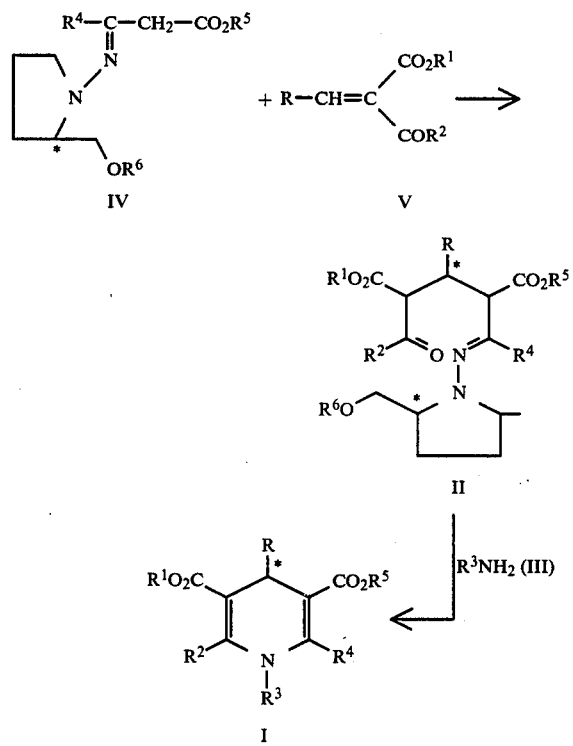

in which optically pure products are obtained. The process is novel, as is II. I is known as being active on the blood circulation system.

2 Claims; No Drawings

INTERMEDIATES OF OPTICALLY ACTIVE 1,4-DIHYDROPYRIDINES

The present invention relates to a novel process for the preparation of optically active 1,4-dihydropyridine derivatives.

It has already been disclosed that certain 1,4-dihydropyridine derivatives have interesting pharmacological properties and are used, in particular, as agents which influence the circulation (compare F. Bossert and W. Vater, Naturwissenschaften 58, 578 (1971) and DE-OS (German Published Specification) No. 2,117,571).

It is furthermore already known that the antipodes of chiral 1,4-dihydropyridine-3,5-dicarboxylic acid esters can be prepared by various processes (DE-OS (German Published Specification) No. 2,935,451; T. Shibanuma et al. Chem. Pharm. Bull. 28, 2809 (1980); and DE-OS (German Published Specification) No. 3,320,616).

The present invention relates to a new, chemically peculiar process for the preparation of optical antipodes of chiral 1,4-dihydropyridine-3,5-dicarboxylic acid esters.

It has been found that the antipodes, some of which are known, of chiral 1,4-dihydropyridine-dicarboxylic acid esters of the general formula (I)

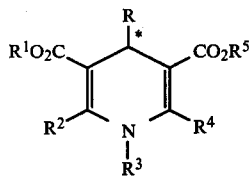

in which

R represents carbocyclic aryl or a heterocyclic radical from the group comprising thienyl, furyl, pyrryl, pyrazolyl, imidazolyl, oxazolyl, isoxazolyl, thiazolyl, pyridyl, pyridazinyl, pyrimidyl, pyrazinyl, indolyl, benzimidazolyl, benzoxazolyl, benzoxadiazolyl, benzothiadiazolyl, quinolyl, isoquinolyl, quinazolyl and quinoxalyl, the aryl radical and the heterocyclic radicals optionally containing 1 to 3 identical or different substituents from the group comprising phenyl, alkyl, alkoxy, alkylene, dioxyalkylene, halogen, polyfluoroalkyl, polyfluoroalkoxy, alkylamino, nitro, cyano, azido, alkoxycarbonyl or $SO_m$-alkyl (m=0 to 2), $R^1$ and $R^5$ are always different and represent an achiral straight-chain, branched or cyclic, saturated or unsaturated hydrocarbon radical, which is optionally interrupted in the chain by an oxygen or sulphur atom, and/or which is optionally substituted by halogen, cyano, alkoxycarbonyl, phenyl, phenoxy, phenylthio or phenylsulphonyl, it being possible for the phenyl groups in turn to be substituted by halogen, cyano, dialkylamino, alkoxy, alkyl, trifluoromethyl or nitro, or it being possible for the hydrocarbon radical to be substituted by pyridyl or an amino group, this amino group being substituted by two identical or different substituents from the group comprising alkyl, alkoxyalkyl, aryl and aralkyl, or the amino group being substituted such that two substituents, together with the nitrogen atom, form a 5-membered to 7-membered ring, which can contain, as a further heteroatom, oxygen or sulphur or an N-alkyl/phenyl grouping, $R^2$ and $R^4$ can be identical or different and each represent hydrogen, an achiral straight-chain or branched, optionally substituted alkyl radical, an aryl radical or an aralkyl radical and $R^3$ represents hydrogen or an achiral straight-chain or branched alkyl radical, an aryl radical or an aralkyl radical, are obtained by a process in which the compounds of the general formula (II) (including their prototropic forms)

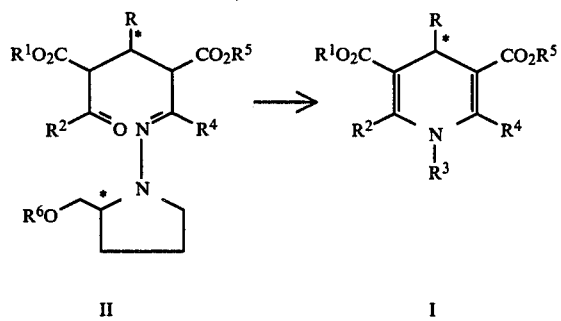

in which the radicals R, $R^1$, $R^2$, $R^4$ and $R^5$ have the abovementioned meaning and $R^6$ represents an alkyl or aralkyl radical, and in which the configuration at the carbon atoms designated (*) is defined as uniform, are reacted with amines of the general formula (III)

$$R^3\text{—}NH_2 \qquad (III)$$

or acid addition salts thereof, in which $R^3$ has the abovementioned meaning, if appropriate in the presence of suitable solvents.

An essential advantage of the process is that, because of its simple reaction conditions, it can be carried out with little technical effort and high profitability, and particular reference should be made to the fact that (S)- or (R)-1-amino-2-alk(aralk)oxymethyl-pyrrolidine is liberated again during the reaction and can be reintroduced into the reaction process as the chiral inductor.

The preparation of an optically active ethyl isopropyl 1,4-dihydro-2,6-dimethyl-4-(3-nitrophenyl)pyridine-3,5-dicarboxylate can be represented by way of example by the following equation:

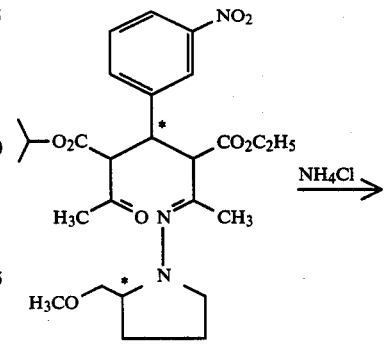

-continued

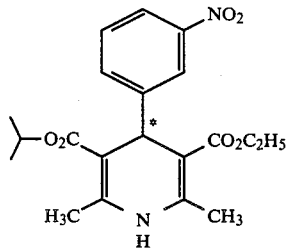

In the process according to the invention, an optically active 1,4-dihydropyridine derivative of the general formula (I) is obtained by reacting an optically active hydrazone of uniform configuration, of the general formula (II), with an amine, or acid addition salt thereof, of the general formula (III), if appropriate in the presence of a suitable solvent.

Preferably, in formulae (I) and (II),

R represents a phenyl or naphthyl radical, or represents thienyl, furyl, pyrryl, pyrazolyl, imidazolyl, oxazolyl, isoxazolyl, thiazolyl, pyridyl, pyridazinyl, pyrimidyl, pyrazinyl, indolyl, benzimidazolyl, benzoxazolyl, benzisoxazolyl, benzoxadiazolyl, benzothiadiazolyl, quinolyl, isoquinolyl, quinazolyl or quinoxalyl, it being possible for the heterocyclic radicals mentioned and the phenyl radical and naphthyl radical to carry 1 to 3 identical or different substituents, substituents which may be mentioned being phenyl, straight-chain or branched alkyl with up to 8 carbon atoms, cycloalkyl with 3 to 7 carbon atoms, alkenyl or alkinyl with 2 to 6 carbon atoms, alkoxy with 1 to 4 carbon atoms, alkenoxy and alkinoxy with 2 to 6 carbon atoms, tri-, tetra- and penta-methylene, dioxymethylene, dioxyethylidene, halogen, such as fluorine, chlorine, bromine or iodine, trifluoromethyl, trifluoroethyl, trifluoromethoxy, difluoromethoxy, tetrafluoroethoxy, dialkylamino with 1 to 4 C atoms, nitro, cyano, azido, alkoxycarbonyl with 1 to 4 C atoms in the alkoxy radical and $SO_m$-alkyl, m denoting 0 or 2 and alkyl containing 1 to 4 carbon atoms.

Preferably, furthermore, in the formulae (I) and (II), $R^1$ and $R^5$, which are always different, represent an achiral straight-chain, branched or cyclic, saturated or unsaturated hydrocarbon radical with up to 8 carbon atoms, which is optionally interrupted in the chain by an oxygen or sulphur atom, and/or which is optionally substituted by halogen, such as fluorine or chlorine, cyano, alkoxycarbonyl with up to 4 carbon atoms in the alkyl part, phenyl, phenoxy, phenylthio or phenylsulphonyl, it being possible for the phenyl groups in turn to be substituted by halogen, such as fluorine or chlorine, cyano, dialkylamino with up to 4 carbon atoms per alkyl group, alkoxy or alkyl with in each case up to 4 carbon atoms, trifluoromethyl or nitro, or it being possible for the hydrocarbon radical to be substituted by pyridyl or an amino group, this amino group being substituted by two identical or different substituents from the group comprising alkyl with up to 4 carbon atoms, alkoxyalkyl with up to 6 carbon atoms, aryl, in particular phenyl, and aralkyl, in particular benzyl, or it being possible for the amino group to be substituted such that two radicals, together with the nitrogen atom, form a 5-membered to 7-membered heterocyclic ring, which can contain, as a further hetero-atom, oxygen or sulphur or an N-alkyl phenyl grouping, and $R^2$ and $R^4$ can be identical or different and represent hydrogen or, preferably, a straight-chain or branched, optionally substituted alkyl radical with up to 4 carbon atoms, a phenyl or a benzyl radical.

Furthermore, in formula II, $R^6$ preferably represents an achiral straight-chain or branched alkyl radical with up to 4 carbon atoms, in particular the methyl group, or an aralkyl radical, in particular the benzyl radical.

The compounds of the general formula (II) are new and can be obtained by processes analogous to those known from the literature, by addition of an optically active hydrazone of the (S)- or (R)-1-amino-2-alk(aralk-)oxymethyl-pyrrolidine of the general formula (IV), including its prototropic forms, onto stereochemically uniform

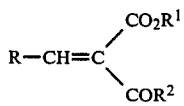

prochiral ylidene-$\beta$-keto-carboxylic acid esters of the general formula (V) (compare D. Enders and K. Papdopoulos, Tetrahedron Letters 24, 4967 (1983)). In formulae (IV) and (V), the radicals R, $R^1$, $R^2$, $R^4$, $R^5$ and $R^6$ have the abovementioned meaning.

In formulae (I) and (III), $R^3$ preferably represents hydrogen or an archiral straight-chain or branched alkyl radical with up to 4 carbon atoms, a phenyl radical or a benzyl radical.

The amines of the formula (III), and acid addition salts thereof, used as starting compounds are known. Possible acid addition salts are the salts of both inorganic and organic acids, hydrogen halide acids, sulphuric acid, carbonic acid and acetic acid being mentioned as examples.

Salts which may be mentioned in particular are ammonium and methylammonium sulphates, chlorides, carbonates, bicarbonates, acetates and oxalates.

Diluents which can be used are all the inert organic solvents. These include, preferably, alcohols, such as methanol or ethanol, ethers, such as tetrahydrofuran, glycol monomethyl ether or glycol dimethyl ether, glacial acetic acid, dimethylformamide, dimethylsulphoxide, acetonitrile, pyridine or hexamethylphosphoric acid triamide.

The reaction temperatures can be varied within a substantial range. In general, the reaction is carried out between 0° and 150° C., preferably between 20° and 100° C., and in particular at the boiling point of the particular solvent.

The reaction can be carried out under normal pressure, but also under increased pressure. In general, the reaction is carried out under normal pressure.

In carrying out the process according to the invention, 1 mole of the hydrazone of the general formula (II) is reacted with 1 to 5 moles of the amine of the general formula (III), or acid addition salts thereof, in a suitable solvent.

The end products are preferably isolated and purified by a procedure in which the solvent is distilled off in vacuo and, if appropriate, the residue is subjected to the purification operations known from the prior art, such as recrystallization from a suitable solvent or chromatographic separation.

The process according to the invention is suitable for the preparation of the optical antipodes of chiral 1,4-dihydropyridine-3,5-dicarboxylic acid esters with a broad spectrum of substituents and structural variations.

Apart from the preparation examples given below, the enantiomers of the following active compounds may be mentioned in particular: isobutyl methyl 1,4-dihydro-2,6-dimethyl-4-(3-nitrophenyl)-pyridine-3,5-dicarboxylate, methyl neopentyl 1,4-dihydro-2,6-dimethyl-4-(3-nitrophenyl)-pyridine-3,5-dicarboxylate, cyclopentyl methyl 1,4-dihydro-2,6-dimethyl-4-(3-nitrophenyl)-pyridine-3,5-dicarboxylate, isopropyl 2-methoxyethyl 1,4-dihydro-2,6-dimethyl-4-(3-nitrophenyl)-pyridine-3,5-dicarboxylate, methyl 2-N-benzyl-N-methylaminoethyl 1,4-dihydro-2,6-dimethyl-4-(3-nitrophenyl)-pyridine-3,5-dicarboxylate, methyl 2-(4-phenyl-piperazin-1-yl)-ethyl 1,4-dihydro-2,6-dimethyl-4-(3-nitrophenyl)-pyridine-3,5-dicarboxylate, benzyl methyl 1,4-dihydro-2,6-dimethyl-4-(2-nitrophenyl)-pyridine-3,5-dicarboxylate, methyl 2-phenoxyethyl 1,4-dihydro-2,6-dimethyl-4-(2-nitrophenyl)-pyridine-3,5-dicarboxylate, isopropyl methyl 1,4-dihydro-2,6-dimethyl-4-(2-trifluoromethylphenyl)-pyridine-3,5-dicarboxylate, allyl methyl 1,4-dihydro-2,6-dimethyl-4-(2-chlorophenyl)-pyridine-3,5-dicarboxylate, ethyl methyl 1,4-dihydro-2,6-dimethyl-4-(2,3-dichlorophenyl)-pyridine-3,5-dicarboxylate, hexyl methyl 1,4-dihydro-2,6-dimethyl-4-(2,3-dichlorophenyl)-pyridine-3,5-dicarboxylate, methyl 2,2,2-trifluoroethyl 1,4-dihydro-2,6-dimethyl-4-(2-chlorophenyl)-pyridine-3,5-dicarboxylate, ethyl 2,2,2-trifluoroethyl 1,4-dihydro-2,6-dimethyl-4-(2-chlorophenyl)-pyridine-3,5-dicarboxylate, ethyl methyl 1,4-dihydro-2,6-dimethyl-4-(2-cyanophenyl)-pyridine-3,5-dicarboxylate, ethyl methyl 1,4-dihydro-2,6-dimethyl-4-(pyrid-3-yl)-pyridine-3,5-dicarboxylate, cyclohexyl methyl 1,4-dihydro-2,6-dimethyl-4-(pyrid-2-yl)-pyridine-2,5-dicarboxylate, isopropyl methyl 1,4-dihydro-2,6-dimethyl-4-(2,1,3-benzoxadiazol-4-yl)-pyridine-3,5-dicarboxylate, ethyl methyl 1,4-dihydro-2,6-dimethyl-4-(2,1,3-benzoxadiazol-4-yl)-pyridine-3,5-dicarboxylate, isopropyl methyl 1,4-dihydro-1,2,6-trimethyl-4-(2,1,3-benzoxadiazol-4-yl)-pyridine-3,5-dicarboxylate, ethyl methyl 1,4-dihydro-1,2,6-trimethyl-4-(3-nitrophenyl)-pyridine-3,5-dicarboxylate and isobutyl methyl 1,4-dihydro-1,2,6-trimethyl-4-(2-nitrophenyl)-pyridine-3,5-dicarboxylate.

PREPARATION EXAMPLES

EXAMPLE 1

Ethyl methyl (-)-1,4-dihydro-2,6-dimethyl-4-(3-nitrophenyl)-pyridine-3,5-dicarboxylate

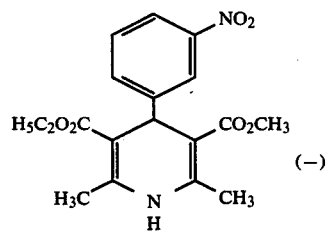

After addition of 25 ml of tetramethylethylenediamine, 28 ml (44.8 mmol) of a 1.6 molar BuLi solution in h-hexane were added dropwise to a solution of 10 g (43.8 mmol) of methyl (S)-3-[(2-methoxy-methylpyrrolidin-1-yl)-imino]-butyrate in 90 ml of absolute tetrahydrofuran at −70° C. under nitrogen. A solution of 11.5 g (43.8 mmol) of ethyl 2-(3-nitrobenzylidene)-acetoacetate in 75 ml of tetrahydrofuran was then added dropwise at −70° C. After the mixture had been stirred at −70° C. for one hour, the cooling bath was removed and the reaction solution was left to stand until it had reached room temperature (about 3 to 4 hours) and then carefully poured into ether/water. The aqueous phase was extracted with ether again and, after drying over anhydrous sodium sulphate, the combined ethereal extracts were concentrated in vacuo, which resulted in an oily residue (15 g, $M^{\oplus}=491$), which was purified by chromatography. 12 g (24 mmol) of this intermediate were taken up in 50 ml of methanol and, after addition of 3.2 g (60 mmol) of ammonium chloride, the mixture was heated at the boiling point for 15 hours. The solvent was then distilled off in vacuo, the residue was taken up in methylene chloride and the mixture was washed with water. The organic phase was concentrated, after drying over NaSO$_4$. The oil which remained partly crystallized out after trituration with ether, and the crude product was filtered off with suction, washed with ether and dried; 3.3 g (38%), melting point: 159° C.

$[\alpha]_D^{20} = -14.97°$ (C=0.57%, ethanol).

EXAMPLE 2

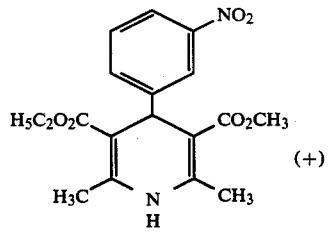

Dextrorotatory ethyl methyl 1,4-dihydro-2,6-dimethyl-4-(3-nitrophenyl)-pyridine-3,5-dicarboxylate was obtained analogously to Example 1 using methyl (R)-3-[(2-methoxymethylpyrrolidin-1-yl)-imino]-butyrate.

Melting point: 160° C., $[\alpha]_D^{20} = +15.56$ (C=0.41%, ethanol).

EXAMPLE 3

Isopropyl methyl
(-)-1,4-dihydro-2,6-dimethyl-4-(3-nitrophenyl)-pyridine-3,5-dicarboxylate

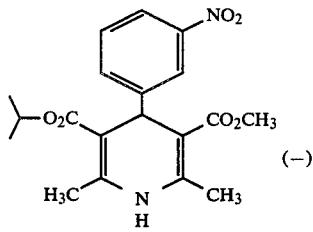

After addition of 20 ml of tetramethylethylenediamine, 20 ml (32 mmol) of a 1.6 molar solution of butyllithium in n-hexane were added dropwise to a solution of 7.1 g (31 mmol) of methyl (S)-3-[(2-methoxymethylpyrrolidin-1-yl)-imino]-butyrate in 60 ml of absolute tetrahydrofuran at −70° C. under nitrogen. A solution of 8.6 g (31 mmol) of isopropyl 2-(3-nitrobenzylidene)-acetoacetate in 40 ml of tetrahydrofuran was then added dropwise at −70° C. The reaction mixture was stirred at −70° C. for 1 hour, the cooling bath was then removed and, when the solution had reached room temperature (about 3 to 4 hours), it was slowly poured into ether/water. The aqueous phase was extracted several times with ether and the combined organic extracts were dried over anhydrous sodium sulphate. Evaporation of the solvent in vacuo gave an oily intermediate (12 g, $M^{\oplus}=505$), which was purified by chromatography. 8 g (15.8 mmol) of this compound were dissolved in 50 ml of methanol and, after addition of 3.4 g (64 mmol) of ammonium chloride, the mixture was heated under reflux for 16 hours. The solvent was distilled off in vacuo, the residue was taken up in methylene chloride and the mixture was washed with water. The organic phase was dried over anhydrous sodium sulphate and concentrated in vacuo and the oily residue was made to crystallize by trituration with a little ether. The solid product was filtered off with suction and dried; 2.3 g (39%), melting point: 136° C.

$[\alpha]_D^{20} = -24.60°$ (C=1.07%, ethanol).

EXAMPLE 4

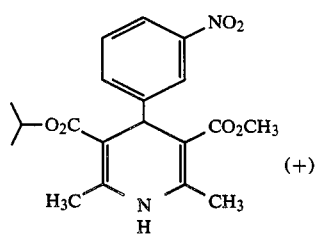

Dextrorotatory isopropyl methyl 1,4-dihydro-2,6-dimethyl-4-(3-nitrophenyl)-pyridine-3,5-dicarboxylate was obtained analogously to Example 3 using methyl (R)-3-[(2-methoxymethylpyrrolidon-1-yl)-imino]-butyrate.

Melting point: 136° C.

$[\alpha]_D^{20} = +24.97°$ (C=0.93%, ethanol).

EXAMPLE 5

Isobutyl methyl
(-)-1,4-dihydro-2,6-dimethyl-4-(2-nitrophenyl)-pyridine-3,5-dicarboxylate

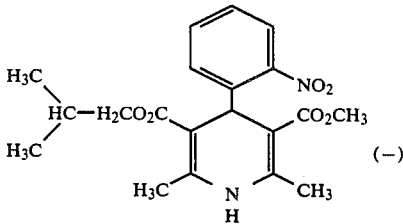

After addition of 20 ml of tetramethylethylenediamine, 20 ml (32 mmol) of a 1.6 molar solution of butyllithium in n-hexane were added dropwise to a solution of 7.1 g (31 mmol) of methyl (S)-3-[(2-methoxymethylpyrrolidin-1-yl)-imino]-butyrate in 60 ml of absolute tetrahydrofuran at −70° C. under nitrogen. A solution of 9 g (31 mmol) of isobutyl 2-(2-nitrobenzylidene)-acetoacetate in 50 ml of tetrahydrofuran was then added dropwise at −70° C., and the solution was stirred for a further hour at −70° C. The cooling bath was removed and, after the solution had reached room temperature (about 3 to 4 hours), it was slowly poured into ether/water. The aqueous phase was extracted again with ether and the combined organic extracts were dried over anhydrous sodium sulphate. Removal of the solvent by distillation in vacuo gave an oily intermediate (12.8 g, $M^{\oplus}=/519$), which was purified by chromatography over silica gel.

6.4 g (12.3 mmol) of this compound were dissolved in 25 ml of methanol and, after addition of 1.61 g (30.2 mmol) of ammonium chloride, the mixture was heated under reflux for 15 hours. The solvent was distilled off in vacuo, the residue was taken up in methylene chloride and the mixture was washed with water. The organic phase was dried over anhydrous sodium sulphate and concentrated in vacuo and the oily residue was purified by chromatography to give 1.4 g (30%) of an amorphous product.

$[\alpha]_D^{20} = -166.4°$ (0.49% w/v, ethanol).

EXAMPLE 6

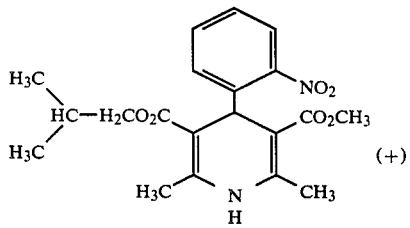

Dextrorotatory isobutyl methyl 1,4-dihydro-2,6-dimethyl-4-(2-nitrophenyl)-pyridine-3,5-dicarboxylate was obtained analogously to Example 5 using methyl (R)-3-[(2-methoxymethylpyrrolidin-1-yl)-imino]-butyrate.

$[\alpha]_D^{20} = +166.3°$ (0.68% w/v, ethanol).

It will be understood that the specification and examples are illustrative but not limitative of the present invention and that other embodiments within the spirit

What is claimed is:

1. A compound of the formula

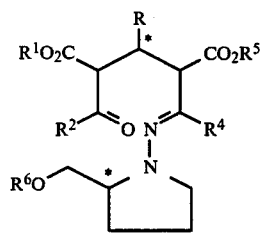

in which

R represents carbocylic aryl or a heterocylic radical from the group consisting of thienyl, furyl, pyrryl, pyrazolyl, imidazolyl, oxazolyl, isoxazolyl, thiazolyl, pyridyl, pyridazinyl, pyrimidyl, pyrazinyl, indolyl, benzimidazolyl, benzoxazolyl, benzoxadiazolyl, benzothiadiazolyl, quinolyl, isoquinolyl, quinazolyl, and quinoxazolyl, the aryl radical and the heterocyclic radicals optionally containing 1 to 3 identical or different substituents from the group consisting of phenyl, alkyl, cycloalkyl, alkenyl, alkinyl, alkoxy, alkenoxy, alkinoxy, alkylene, dioxyalkylene, halogen, polyfluoroalkyl, polyfluoroalkoxy, alkylamino, dialkylamino, nitro, cyano, azido, alkoxycarbonyl or $SO_m$-alkyl (m=0 to 2), $R^1$ and $R^5$ are always different and represent an achiral straight-chain, branched or cyclic, saturated or unsaturated hydrocarbon radical, which is optionally interrupted in the chain by an oxygen or sulphur atom, and/or which is optionally substituted by halogen, cyano, alkoxycarbonyl, phenyl, phenoxy, phenylthio or phenylsulphonyl, it being possible for the phenyl groups in turn to be substituted by halogen, cyano, dialkylamino, alkoxy, alkyl, trifluoromethyl or nitro, or it being possible for the hydrocarbon radical to be substituted by pyridyl or an amino group, this amino group being substituted by two identical or different substituents from the group consisting of alkyl, alkoxyalkyl, carbocyclic aryl and aralkyl, or the amino group being substituted such that two substituents, together with the nitrogen atom, form a 5-member to 7-membered ring, which can contain, as a further hetero-atom, oxygen or sulphur or an N-alkyl/phenyl grouping, $R^2$ and $R^4$ can be identical or different and each represent hydrogen, an achiral straight-chain or branched, optionally substituted alkyl radical and a carbocyclic aryl radical or a carbocyclic aryl radical or a carbocylic aralkyl radical and $R^6$ represents an achiral straight-chain or branched alkyl radical with up to 4 carbon atoms or a carbocylic aralkyl radical.

2. A compound according to claim 1, in which

R represents a phenyl or naphthyl radical, or represents thienyl, furyl, pyrryl, pyrazolyl, imidazolyl, oxazolyl, isoxazolyl, thiazolyl, pyridyl, pyridazinyl, pyrimidyl, pyrazinyl, indolyl, benzimidazolyl, benzoxazolyl, benzisoxazolyl, benzoxadiazolyl, benzothiadiazolyl, quinolyl, isoquinolyl, quinazolyl or quinoxalyl, it being possible for the heterocyclic radicals mentioned and the phenyl radical and naphthyl radical to carry 1 to 3 identical or different substituents selected from phenyl, straight-chain or branched alkyl with up to 8 carbon atoms, cycloalkyl with 3 to 7 carbon atoms, alkenyl or alkinyl with 2 to 6 carbon atoms, alkoxy with 1 to 4 carbon atoms, alkenoxy and alkinoxy with 2 to 6 carbon atoms, tri-, tetra- and penta-methylene, dioxymethylene, dioxyethylidene, halogen, trifluoromethyl, trifluoroethyl, trifluoromethoxy, difluoromethoxy, tetrafluoroethoxy, dialkylamino with 1 to 4 C atoms, nitro, cyano, azido, alkoxycarbonyl with 1 to 4 C atoms in the alkoxy radical and $SO_m$-alkyl, m denoting 0 or 2 and alkyl containing 1 to 4 carbon atoms, $R^1$ and $R^5$, which are always different, represent an achiral straight-chain, branched or cyclic, saturated or unsaturated hydrocarbon radical with up to 8 carbon atoms, which is optionally interrupted in the chain by an oxygen or sulphur atom, and/or which is optionally substituted by halogen, cyano, alkoxycarbonyl with up to 4 carbon atoms in the alkyl part, phenyl, phenoxy, phenylthio or phenylsulphonyl, it being possible for the phenyl groups in turn to be substituted by halogen, cyano, dialkylamino with up to 4 carbon atoms per alkyl group, alkoxy or alkyl with in each case up to 4 carbon atoms, trifluoromethyl or nitro, or it being possible for the hydrocarbon radical to be substituted by pyridyl or an amino group, this amino group being substituted by two identical or different substituents from the group consisting of alkyl with up to 4 carbon atoms, alkoxyalkyl with up to 6 carbon atoms, carbocyclic aryl and aralkyl, or it being possible for the amino group to be substituted such that two radicals, together with the nitrogen atom, form a 5-membered to 7-membered heterocyclic ring, which can contain, as a further hetero-atom, oxygen or sulphur or an N-alkyl phenyl grouping, $R^2$ and $R^4$ can be identical or different and represent hydrogen or a straight-chain or branched, optionally substituted alkyl radical with up to 4 carbon atoms, a phenyl or a benzyl radical and $R^6$ represents an achiral straight-chain or branched alkyl radical with up to 4 carbon atoms or a carbocyclic aralkyl radical.

* * * * *